United States Patent
Huang et al.

(10) Patent No.: US 11,912,596 B2
(45) Date of Patent: Feb. 27, 2024

(54) APPLICATION OF HYDROPHOBIC PHTHALOCYANINE AS HETEROGENEOUS CATALYST IN OXIDIZING PHENOL WASTEWATER BY HYDROGEN PEROXIDE

(71) Applicant: Hangzhou Normal University, Hangzhou (CN)

(72) Inventors: Jiachi Huang, Hangzhou (CN); Shiliang Chen, Hangzhou (CN)

(73) Assignee: Hangzhou Normal University, Hangzhou (CN)

( * ) Notice: Subject to any disclaimer, the term of this patent is extended or adjusted under 35 U.S.C. 154(b) by 0 days.

(21) Appl. No.: 18/473,194

(22) Filed: Sep. 22, 2023

(65) Prior Publication Data
US 2024/0010530 A1    Jan. 11, 2024

Related U.S. Application Data

(62) Division of application No. 17/980,428, filed on Nov. 3, 2022, now Pat. No. 11,807,559.

(30) Foreign Application Priority Data

Feb. 21, 2022    (CN) .......................... 202210156583.1

(51) Int. Cl.
*C02F 1/72*    (2023.01)
*B01J 31/18*    (2006.01)
(Continued)

(52) U.S. Cl.
CPC .............. *C02F 1/725* (2013.01); *B01J 31/183* (2013.01); *B01J 31/28* (2013.01); *B01J 37/36* (2013.01);
(Continued)

(58) Field of Classification Search
CPC .... C02F 1/725; C02F 1/722; C02F 2305/023; C02F 2101/345; B01J 31/183; B01J 37/36; B01J 31/28; B01J 2231/70
See application file for complete search history.

(56) References Cited

FOREIGN PATENT DOCUMENTS

| CN | 101747443 A | * | 6/2010 | ............. C08B 15/00 |
| CN | 101747443 A | | 6/2010 | |

(Continued)

OTHER PUBLICATIONS

Wu et al. (Efficient Catalytic Degradation of Phenol with Phthalocyanine-Immobilized Reduced Graphene—Bacterial Cellulose Nanocomposite, Aug. 28, 2021, Nanomaterials 2021, 11, 2218. https://doi.org/10.3390/nano11092218). (Year: 2021).*

(Continued)

*Primary Examiner* — Youngsul Jeong

(57) ABSTRACT

Disclosed is a method for treating phenol wastewater. The method includes the following step: adding a hydrophobic phthalocyanine as a catalyst, and $H_2O_2$ as an oxidant into the phenol wastewater. The hydrophobic phthalocyanine is obtained by decorating a hydrophobic group on a bacterial cellulose-metal phthalocyanine with a silane coupling agent; the bacterial cellulose-metal phthalocyanine is obtained by mixing a metal phthalocyanine into a bacterial cellulose medium, biologically culturing with an acetic acid bacterium, and then heating and reducing the mixture; and the metal phthalocyanine is nitro-sulfonic metal phthalocyanine.

7 Claims, 1 Drawing Sheet

(51) Int. Cl.
 *B01J 31/28* (2006.01)
 *B01J 37/36* (2006.01)
 *C02F 101/34* (2006.01)

(52) U.S. Cl.
 CPC ........... *C02F 1/722* (2013.01); *B01J 2231/70* (2013.01); *C02F 2101/345* (2013.01); *C02F 2305/023* (2013.01)

(56) References Cited

FOREIGN PATENT DOCUMENTS

| | | | | |
|---|---|---|---|---|
| CN | 109797450 A | | 5/2019 | |
| CN | 111229325 A | * | 6/2020 | ............ B01J 31/183 |
| CN | 111229325 A | | 6/2020 | |
| CN | 111298840 A | * | 6/2020 | ............ B01J 31/183 |
| CN | 111298840 A | | 6/2020 | |
| CN | 111484517 A | | 8/2020 | |
| CN | 113318790 A | * | 8/2021 | .............. B01J 31/22 |
| CN | 113318790 A | | 8/2021 | |

OTHER PUBLICATIONS

CN-113318790-A_English (Year: 2021).*
CN-111229325-A_English (Year: 2020).*
CN-101747443-A_English (Year: 2010).*
CN-111298840-A_English (Year: 2020).*

* cited by examiner

APPLICATION OF HYDROPHOBIC PHTHALOCYANINE AS HETEROGENEOUS CATALYST IN OXIDIZING PHENOL WASTEWATER BY HYDROGEN PEROXIDE

CROSS REFERENCE TO RELATED APPLICATIONS

This application is a continuation of U.S. patent application Ser. No. 17/980,428, filed on Nov. 3, 2022, entitled "Application of hydrophobic phthalocyanine as heterogeneous catalyst in oxidizing phenol wastewater by hydrogen peroxide," which claims foreign priority of China Patent Application No. 202210156583.1, filed on Feb. 21, 2022 in the China National Intellectual Property Administration (CNIPA), the entire contents of which are hereby incorporated by reference in their entireties.

TECHNICAL FIELD

The present invention belongs to the technical field of organic wastewater treatment; and particularly relates to a method for treating phenol wastewater.

BACKGROUND

Metal phthalocyanine compounds are functional micromolecules with excellent properties, and a series of metal phthalocyanine derivatives with special physical and chemical properties can be obtained by changing the central metal atom and outer ring substituents thereof. Due to excellent chemical, optical and electrical properties, the metal phthalocyanine compounds may be applied to optical sensing materials, nonlinear optical materials, solar cell materials, fuel cells and other different fields. In particular, the structure of the metal phthalocyanine is highly similar to that of metalloporphyrin, the active center of active molecules such as chlorophyll and heme in nature. Inspired by this, researchers tried to apply the metal phthalocyanine to different catalytic reactions, and achieved remarkable achievements. In practice, in order to reuse the metal phthalocyanine, researchers often fix the metal phthalocyanine on solid carrier materials to prepare heterogeneous metal phthalocyanine catalysts. This technology can not only separate the metal phthalocyanine from the reaction system conveniently, but also reduce the problem of low catalytic activity caused by the formation of low-activity aggregates between phthalocyanine molecules, and avoid the secondary pollution caused by the phthalocyanine molecules entering the environment at the same time. The selection of suitable solid-phase carrier and preparation of heterogeneous metal phthalocyanine catalytic materials by a proper immobilization method have become research hotspots in the field of preparation and catalytic applications of metal phthalocyanine materials.

The application of the metal phthalocyanine in the treatment of organic pollutants and the catalytic oxidation and degradation of the organic pollutants with the help of oxidants (such as hydrogen peroxide ($H_2O_2$)) is one of the key concerns in the field of environmental purification. The basic catalytic degradation mechanism of the organic pollutants by the catalytic system of metal phthalocyanine+$H_2O_2$ is as follows: the metal phthalocyanine and $H_2O_2$ firstly form a metal phthalocyanine-OOH intermediate which would be cracked to form active species such as high valence metal=O and hydroxyl radical, and then the formed active species attack the organic pollutant molecules, finally achieving the object of catalytic oxidation and degradation. In actual reaction, in addition to forming the active species, $H_2O_2$ may also be decomposed into oxygen and water under the action of the metal phthalocyanine-OOH intermediate. The existence of this side reaction reduces the generation efficiency of the active species, and meanwhile, the obviously low utilization of $H_2O_2$ requires a much higher amount of $H_2O_2$ needed than that of a theoretical value in industrial applications. By constructing a suitable reaction micro-environment, the catalytic degradation efficiency of the catalyst for the organic pollutants can be effectively improved by adjusting the concentration of $H_2O_2$ around the metal phthalocyanine catalyst reasonably to reduce the possibility of side reaction with excess $H_2O_2$ after forming the metal phthalocyanine-OOH intermediate and increase the formation of the active species.

Based on the above analysis, it is of obvious application values in the fields of both catalysis and organic wastewater treatment by selecting a suitable metal phthalocyanine solid carrier and using a suitable immobilization method to obtain the heterogeneous metal phthalocyanine catalytic materials, and constructing a suitable reaction micro-environment for the heterogeneous metal phthalocyanine catalytic materials, so that $H_2O_2$ can be effectively utilized to generate the active species while using the heterogeneous metal phthalocyanine catalytic materials to treat industrial organic wastewater such as phenols, and the catalytic reaction efficiency of the catalyst can be improved.

SUMMARY

The object of the present invention is to provide a simple, efficient and green bacterial cellulose-metal phthalocyanine heterogeneous catalyst for oxidative degradation of phenolic industrial wastewater and a preparation method thereof, and then decorate a hydrophobic silane on the bacterial cellulose-metal phthalocyanine heterogeneous catalyst to obtain the hydrophobic phthalocyanine heterogeneous catalyst. With $H_2O_2$ as an oxidant, the hydrophobic phthalocyanine heterogeneous catalyst can efficiently catalyze the oxidative degradation of phenols. During the catalytic degradation of phenols, the obtained hydrophobic phthalocyanine heterogeneous catalyst can adjust a concentration of the hydrogen peroxide oxidant around the catalyst, limit side reactions in the catalytic process, and achieve the object of significantly improving the catalytic degradation efficiency. According to the present invention, the bacterial cellulose is selected as the solid carrier and reducing agent of the metal phthalocyanine, which realizes the immobilization of metal phthalocyanine at the same time of reduction; the possibility of side reactions in the catalytic reaction process is skillfully reduced through the hydrophobic silane, thus significantly improving the catalytic degradation efficiency of the heterogeneous catalysts on organic pollutants.

In a first aspect, the present invention provides an application of oxidizing phenol wastewater by hydrogen peroxide with a hydrophobic phthalocyanine as a heterogeneous catalyst, wherein the hydrophobic phthalocyanine is obtained by decorating a hydrophobic group on a bacterial cellulose-metal phthalocyanine with a silane coupling agent; the bacterial cellulose-metal phthalocyanine is obtained by mixing a metal phthalocyanine into a bacterial cellulose medium, biologically culturing with an acetic acid bacterium, and then heating and reducing the mixture; and the metal phthalocyanine is nitro-sulfonic metal phthalocyanine (with a structure referring to formula 1).

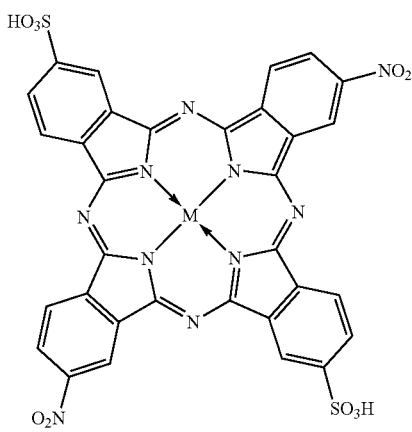

Formula 1: Structural Formula of the Nitro-Sulfonic Metal Phthalocyanine, Wherein a Central Metal M is One of Iron (III) or Cobalt (II)

In a second aspect, the present invention provides a hydrophobic phthalocyanine for catalytic degradation of phenols, wherein the hydrophobic phthalocyanine is obtained by modifying a hydrophobic group on a bacterial cellulose-metal phthalocyanine with a silane coupling agent; the bacterial cellulose-metal phthalocyanine is obtained by mixing a metal phthalocyanine into a bacterial cellulose medium, culturing the mixture with an acetic acid bacterium, and then heating and reducing the mixture; and the metal phthalocyanine is nitro-sulfonic metal phthalocyanine.

Preferably, the process of decorating the hydrophobic group on the bacterial cellulose-metal phthalocyanine is: adding the bacterial cellulose-metal phthalocyanine in a silane coupling agent solution for treatment.

In a third aspect, the present invention provides a preparation method of the fore-mentioned hydrophobic phthalocyanine heterogeneous catalyst for catalytic degradation of phenols, wherein the preparation method comprises the following steps of:

step 1. preparing a mixed solution of a bacterial cellulose medium containing metal phthalocyanine;

step 2. adding an acetic acid bacterium into the mixed solution obtained in step 1 for biological culture;

step 3. heating the product obtained in step 2, and taking out a solid for cleaning and drying;

step 4. preparing a hydrophobic silane coupling agent solution; and step 5. immersing the product obtained in step 3 into the solution obtained in step 4, and taking out a solid after reaction for cleaning and drying to obtain the hydrophobic phthalocyanine.

Preferably, in step 1, the bacterial cellulose medium consists of a glucose, a peptone, a yeast extract and a disodium hydrogen phosphate, wherein concentrations of the glucose, the peptone, the yeast extract and the disodium hydrogen phosphate are 2% to 10%, 0.2% to 1%, 0.2% to 1% and 0.02% to 0.1% respectively; and a concentration of the nitro-sulfonic metal phthalocyanine in the mixed solution is 0.5% to 5%.

Preferably, in step 2, the acetic acid bacterium is one of *Gluconacetobacter intermedius, Acetobacter xylinum* or *Acetobacter hansenii*. Conditions for the biological culture are as follows: a culture temperature ranges from 20° C. to 35° C., and a culture time ranges from 3 days to 10 days.

Preferably, in step 3, the heating is carried out in a temperature range of 80° C. to 99° C. and the reaction time ranges from 12 hours to 72 hours; the cleaning process comprises sequentially cleaning with a hydrochloric acid solution, a sodium hydroxide solution and ultrapure water; a concentration of the hydrochloric acid solution ranges from 0.10 mol/L to 1 mol/L, and a concentration of the sodium hydroxide solution ranges from 0.10 mol/L to 1 mol/L.

Preferably, in step 5, the reaction conditions are as follows: a reaction temperature is 25° C., and a reaction time is 24 hours; and the cleaning process comprises sequentially cleaning with absolute ethyl alcohol and ultrapure water.

Preferably, in step 4, the silane coupling agent is one of trimethoxymethylsilane (CAS No.: 1185-55-3), ethyltrimethoxysilane (CAS No.: 5314-55-6), trimethoxy(propyl)silane (CAS No.: 1067-25-0), trimethoxyphenylsilane (CAS No.: 2996-92-1) or hexadecyltrimethoxysilane (CAS No.: 16415-12-6), the solvent used is toluene, and a concentration range of the hydrophobic silane in the solution is 1 g/L to 50 g/L.

In a fourth aspect, the present invention provides a method for treating phenolic wastewater, comprising the process as follows: adding the hydrophobic phthalocyanine as a catalyst, and $H_2O_2$ as an oxidant into the treated wastewater.

Compared with the prior art, the present invention has the following beneficial effects.

1. In the present invention, the bacterial cellulose-metal phthalocyanine heterogeneous catalyst is modified with the hydrophobic group by the silane coupling agent, and the prepared hydrophobic phthalocyanine heterogeneous catalyst may be used for efficient catalytic degradation of phenolic organic pollutants. Due to the existence of the hydrophobic group, the process of hydrophilic hydrogen peroxide approaching the heterogeneous catalyst is hindered, which makes the concentration of the oxidant around the heterogeneous catalyst reasonably adjusted in the process of phenol catalytic degradation. The decreased side reactions of excess $H_2O_2$ could reduce the likelihood of low utilization and effectively improve the catalytic degradation efficiency of the heterogeneous catalyst on the organic pollutants by increasing the formation of active species. Meanwhile, the hydrophobic phthalocyanine heterogeneous catalyst obtained by the present invention has the advantage of being reusable.

2. The present invention provides a preparation method of a phthalocyanine heterogeneous catalyst. In this method, the bacterial cellulose is selected as the solid carrier and reducing agent of the metal phthalocyanine, which realizes immobilization of the metal phthalocyanine by forming the hydrogen bond between the bacterial cellulose and the amino-sulfonic metal phthalocyanine while reducing the nitro-sulfonic metal phthalocyanine into the amino-sulfonic metal phthalocyanine. Compared with other preparation methods, the preparation method provided by the present invention omits the process of additionally using a chemical reducing agent to convert the nitro-sulfonic metal phthalocyanine into the amino-sulfonic metal phthalocyanine in the prior art, and enables the amino-sulfonic metal phthalocyanine to be fully and uniformly loaded on the bacterial cellulose, and has the advantages of simple preparation process, green preparation process, economy, high efficiency and the like.

3. According to the present invention, the metal phthalocyanine is added into the bacterial cellulose medium and then loads on the bacterial cellulose while the acetic acid bacterium produce the bacterial cellulose. In this process, since the bacterial cellulose continues to grow, the position of the metal phthalocyanine originally loaded on the surface of the bacterial cellulose is changed to the interior of the bacterial cellulose. However, the surface of the grown bacterial cellulose continues to be loaded with the metal phthalocyanine, so that the surface and the interior of the bacterial cellulose are both uniformly loaded with the metal phthalocyanine. Therefore, a large number of catalytic active sites are formed in the interior of the bacterial cellulose due to the ultra-high specific surface area and three-dimensional network structure of the bacterial cellulose, thus significantly improving the catalytic activity of the prepared catalyst.

DETAILED DESCRIPTION

Figure 1:
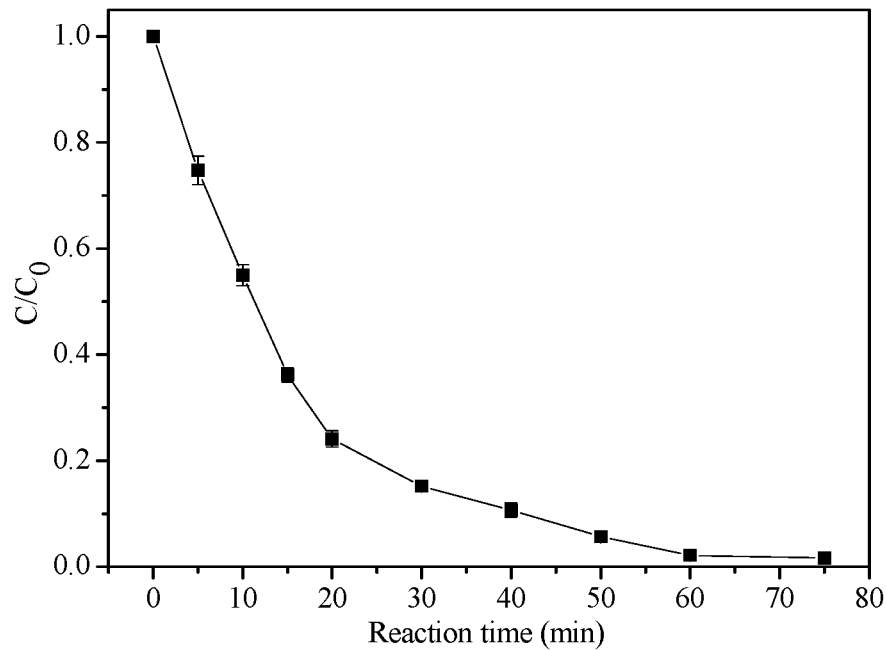
FIG. 1 is a curve showing a change of a phenol solution concentration with a reaction time under the action of a hydrophobic phthalocyanine heterogeneous catalyst provided by the present invention.

The technical solutions in the present invention will be described clearly and completely below. Apparently, the described embodiments are merely some but not all of the embodiments of the present invention. Based on the embodiments of the present invention, all other embodiments obtained by those of ordinary skills in the art without going through any creative work shall fall within the protection scope of the present invention.

Embodiment 1

A preparation method of a hydrophobic phthalocyanine heterogeneous catalyst for catalytic degradation of phenols, comprised the following steps.
(1) 12.00 g of glucose, 1.25 g of peptone, 1.25 g of yeast extract and 0.10 g of disodium hydrogen phosphate were dissolved in 100 mL of ultrapure water, and then added with 2.50 g of nitro-sulfonic iron phthalocyanine to prepare a mixed solution of a bacterial cellulose medium containing metal phthalocyanine.
(2) An acetic acid bacterium was added into the mixed solution obtained in step (1) and cultured for 7 days at 30° C.
(3) The product obtained in step (2) was heated to 90° C. for 24 hours, and the nitro-sulfonic iron phthalocyanine was reduced to amino-sulfonic iron phthalocyanine with the reaction of bacterial cellulose. The metal phthalocyanine was immobilized on the bacterial cellulose by forming a hydrogen bond between the bacterial cellulose and the amino-sulfonic iron phthalocyanine. The solid product was taken out, and cleaned with 0.20 mol/L hydrochloric acid, 0.20 mol/L sodium hydroxide and ultrapure water in turn, and then dried to obtain the bacterial cellulose-metal phthalocyanine heterogeneous catalyst.
(4) 0.50 g of hexadecyltrimethoxysilane, served as a silane coupling agent, was dissolved in 50 mL of toluene to prepare a hydrophobic silane solution.
(5) The product obtained in step (3) was immersed in the solution obtained in step (4) and reacted for 24 hours at 25° C. The solid product was taken out, and cleaned with absolute ethyl alcohol and ultrapure water in turn, and then dried to obtain the hydrophobic phthalocyanine heterogeneous catalyst. A content of the metal phthalocyanine in the obtained hydrophobic phthalocyanine heterogeneous catalyst was 118 μmol/g.

Comparative Example 1

Compared with Embodiment 1, step (3) was not carried out in this comparative example, and other steps and conditions were the same as that in Embodiment 1.

A content of the metal phthalocyanine in the finally obtained hydrophobic phthalocyanine heterogeneous catalyst was 36 μmol/g. By comparing the data of Embodiment 1 and Comparative Example 1, it could be seen that less nitro-sulfonic iron phthalocyanine was immobilized on the bacterial cellulose. After the bacterial cellulose reduced the nitro-sulfonic iron phthalocyanine into the amino-sulfonic iron phthalocyanine, hydrogen bond interaction was formed between the hydroxyl group on the bacterial cellulose and the amino group on the amino-sulfonic iron phthalocyanine, which realized efficient immobilization of the amino-sulfonic iron phthalocyanine on the bacterial cellulose, thus obtaining the bacterial cellulose-metal phthalocyanine heterogeneous catalyst.

Comparative Example 2

Compared with Embodiment 1, step (4) and step (5) were not carried out in this comparative example, and other steps and conditions were the same as that in Embodiment 1.

A content of the metal phthalocyanine in the finally obtained bacterial cellulose-metal phthalocyanine heterogeneous catalyst was 118 μmol/g. By comparing the data of Embodiment 1, Comparative Example 1 and Comparative Example 2, it could be seen that the hydrophobizing treatment step did not affect the content of the metal phthalocyanine on the heterogeneous catalyst.

Embodiment 2

The hydrophobic phthalocyanine heterogeneous catalyst obtained in Embodiment 1 was subjected to a catalytic oxidation and degradation performance test, and organic pollutants degraded in the test were phenol organic pollutants. The specific test process was as follows.

1.50 mg of the hydrophobic phthalocyanine heterogeneous catalyst obtained in Embodiment 1 were applied to the catalytic oxidation and degradation of phenol organic pollutants. The specific experimental conditions were as follows: an initial concentration of a phenol solution was $1\times10^{-3}$ mol/L, a volume of the phenol solution was 20 mL, a pH value of the phenol solution was adjusted to 3, a concentration of a $H_2O_2$ oxidant was 50 mmol/L, and a reaction temperature was 50° C. After reaction for 40 minutes, the concentration of the phenol solution decreased by 89.29%. After reaction for 60 minutes, the concentration of the phenol solution decreased by 97.86%. The specific experimental results were shown in FIG. 1, which showed that the obtained hydrophobic phthalocyanine heterogeneous catalyst had excellent catalytic oxidation and degradation performance on the phenol organic pollutants.

Figure 2:
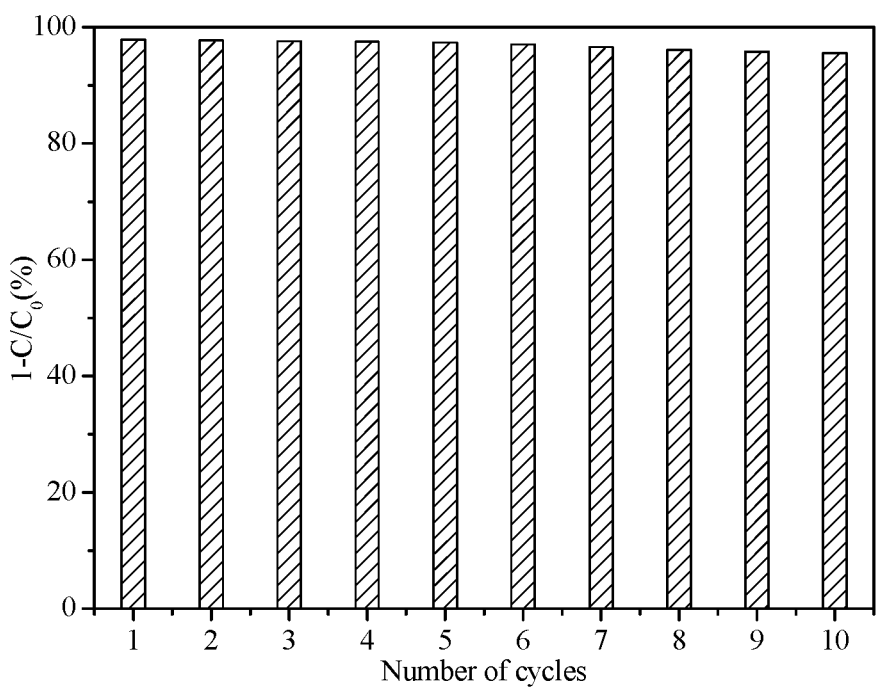
FIG. 2 is a diagram showing a change of a cyclic catalytic degradation performance of the hydrophobic phthalocyanine heterogeneous catalyst provided by the present invention to the phenol solution.

In order to investigate the reusability of the obtained hydrophobic phthalocyanine heterogeneous catalyst, the above-mentioned hydrophobic phthalocyanine heterogeneous catalyst was taken out of the reaction solution, washed with ultrapure water and used again for catalytic oxidation and degradation of the phenol solution under the same experimental conditions. After repeated use for 10 times, the hydrophobic phthalocyanine heterogeneous catalyst could still reduce the concentration of the phenol solution by 95.56% under the same experimental conditions. The specific experimental results were shown in FIG. 2, which showed that the hydrophobic phthalocyanine heterogeneous catalyst had excellent reusability.

Comparative Example 3

1.50 mg of the bacterial cellulose-metal phthalocyanine heterogeneous catalyst obtained in Comparative Example 2 were applied to catalytic oxidation and degradation of phenol organic pollutants. Other experimental conditions were the same as those described in Embodiment 2. After reaction for 40 minutes, the concentration of the phenol solution decreased by 68.27%. After reaction for 60 minutes, the concentration of the phenol solution decreased by 80.66%. It could be seen from Embodiment 2 and Comparative Example 3 that decorating the hydrophobic silane on the bacterial cellulose-metal phthalocyanine heterogeneous catalyst was beneficial to improve the catalytic efficiency of the catalyst.

Embodiment 3

The hydrophobic phthalocyanine heterogeneous catalyst obtained in Embodiment 1 was subjected to a catalytic oxidation and degradation performance test, and organic pollutants degraded in the test were 4-chlorophenol organic pollutants. The specific test process was as follows.

1.50 mg of the hydrophobic phthalocyanine heterogeneous catalyst obtained in Embodiment 1 were applied to the catalytic oxidation and degradation of 4-chlorophenol organic pollutants. The specific experimental conditions were as follows: an initial concentration of a 4-chlorophenol solution was $1\times10^{-3}$ mol/L, a volume of the 4-chlorophenol solution was 20 mL, a pH value of the 4-chlorophenol solution was adjusted to 3, a concentration of a $H_2O_2$ oxidant was 50 mmol/L, and a reaction temperature was 50° C. After reaction for 50 minutes, the concentration of the 4-chlorophenol solution decreased by 92.35%, which showed that the obtained hydrophobic phthalocyanine heterogeneous catalyst also had excellent catalytic oxidation and degradation performance on the 4-chlorophenol organic pollutants.

Comparative Example 4

1.50 mg of the bacterial cellulose-metal phthalocyanine heterogeneous catalyst obtained in Comparative Example 2 were applied to catalytic oxidation and degradation of 4-chlorophenol organic pollutants under the same experimental conditions in Embodiment 3. After reaction for 50 minutes, the concentration of the 4-chlorophenol solution decreased by 62.81%. It could be seen from the data of Embodiment 4 and Comparative Example 3 that modification of the bacterial cellulose-metal phthalocyanine heterogeneous catalyst with the hydrophobic silane was beneficial to improve the catalytic efficiency of the catalyst.

Embodiment 4

A preparation method of a hydrophobic phthalocyanine heterogeneous catalyst for catalytic degradation of phenols, comprised the following steps.

(1) 12.00 g of glucose, 1.25 g of peptone, 1.25 g of yeast extract and 0.10 g of disodium hydrogen phosphate were dissolved in 100 mL of ultrapure water, and then added with 5.00 g of nitro-sulfonic iron phthalocyanine to prepare a mixed solution of a bacterial cellulose medium containing metal phthalocyanine.

(2) An acetic acid bacterium was added into the mixed solution obtained in step (1) and cultured for 7 days at 30° C.

(3) The product obtained in step (2) was heated to 95° C. for 60 hours, and the nitro-sulfonic iron phthalocyanine was reduced to amino-sulfonic iron phthalocyanine with the reaction of bacterial cellulose. The metal phthalocyanine was immobilized on the bacterial cellulose by forming a hydrogen bond between the bacterial cellulose and the amino-sulfonic metal phthalocyanine. The solid product was taken out, and cleaned with 0.20 mol/L hydrochloric acid, 0.20 mol/L sodium hydroxide and ultrapure water in turn, and then dried to obtain the bacterial cellulose-metal phthalocyanine heterogeneous catalyst.

(4) 1.50 g of trimethoxy(propyl)silane were dissolved in 50 mL of toluene to prepare a hydrophobic silane solution.

(5) The product obtained in step (3) was immersed in the solution obtained in step (4) and reacted for 24 hours at 25° C. The solid product was taken out, and cleaned with absolute ethyl alcohol and ultrapure water in turn, and then dried to obtain the hydrophobic phthalocyanine heterogeneous catalyst. A content of the metal phthalocyanine in the obtained hydrophobic phthalocyanine heterogeneous catalyst was 228 μmol/g.

Embodiment 5

The hydrophobic phthalocyanine heterogeneous catalyst obtained in Embodiment 4 was subjected to a catalytic oxidation and degradation performance test, and organic pollutants degraded in the test were phenol organic pollutants. The specific test process was as follows:

1.50 mg of the hydrophobic phthalocyanine heterogeneous catalyst obtained in Embodiment 4 were applied to the catalytic oxidation and degradation of phenol organic pollutants under the same experimental conditions in Embodiment 2. After reaction for 30 minutes, the concentration of the phenol solution decreased by 91.04%.

Embodiment 6

The hydrophobic phthalocyanine heterogeneous catalyst obtained in Embodiment 4 was subjected to a catalytic oxidation and degradation performance test, and organic pollutants degraded in the test were 4-chlorophenol organic pollutants. The specific test process was as follows:

1.50 mg of the hydrophobic phthalocyanine heterogeneous catalyst obtained in Embodiment 4 were applied to the catalytic oxidation and degradation of 4-chlorophenol organic pollutants under the same experimental conditions in Embodiment 4. After reaction for 35 minutes, the concentration of the phenol solution decreased by 92.87%.

The above are only the preferred embodiments of the present invention, so the scope of implementation of the present invention cannot be limited accordingly, that is, the equivalent changes and modifications made according to the patent scope of the present invention and the contents of the specification should still fall within the scope of the present invention.

What is claimed is:

1. A method for treating phenol wastewater, comprising:
adding a hydrophobic phthalocyanine as a catalyst, and $H_2O_2$ as an oxidant into the phenol wastewater, thereby treating the phenol wastewater;
wherein the method further comprising the steps of:
mixing a metal phthalocyanine into a bacterial cellulose medium thereby producing a mixture;
biologically culturing the mixture with an acetic acid bacterium thereby producing a first product mixture;
heating and reducing the first product mixture thereby producing a second product, the second product being a bacterial cellulose-metal phthalocyanine comprising a hydrophobic group; and
decorating the hydrophobic group on the bacterial cellulose-metal phthalocyanine with a silane coupling agent thereby producing the hydrophobic phthalocyanine,
wherein the metal phthalocyanine is nitro-sulfonic metal phthalocyanine.

2. The method according to claim 1, wherein the decorating the hydrophobic group on the bacterial cellulose-metal phthalocyanine is: adding the bacterial cellulose-metal phthalocyanine in a silane coupling agent solution for treatment.

3. The method according to claim 1, wherein the hydrophobic phthalocyanine for the treating phenol wastewater is prepared by a method comprising the following steps of:
S1, preparing a mixed solution of a bacterial cellulose medium containing metal phthalocyanine;
S2, adding an acetic acid bacterium into the mixed solution obtained in S1 for biological culture, thereby producing the first product mixture;
S3, heating the first product mixture obtained in S2 thereby producing a first solid in a heated first product mixture, and taking out the first solid from the heated first product mixture for cleaning and drying, thereby producing a cleaned and dried second product;
S4, preparing a hydrophobic silane coupling agent solution; and
S5, immersing the cleaned and dried second product obtained in S3 into the hydrophobic silane coupling agent solution prepared in S4, thereby conducting a reaction and producing a third product mixture comprising second solid, taking out the second solid from the third product mixture after the reaction, cleaning and drying the second solid, thereafter obtaining a cleaned and dried second solid comprising the hydrophobic phthalocyanine.

4. The method according to claim 3, wherein in S2, the acetic acid bacterium is one of *Gluconacetobacter intermedius, Acetobacter xylinum* or *Acetobacter hansenii*; and conditions for the biological culture are as follows: a culture temperature ranges from 20° C. to 35° C., and a culture time ranges from 3 days to 10 days.

5. The method according to claim 3, wherein in S3, the heating is carried out in a temperature range of 80° C. to 99° C. and a first reaction time ranges from 12 hours to 72 hours; the cleaning comprises sequentially cleaning with a hydrochloric acid solution, a sodium hydroxide solution and ultrapure water; a concentration of the hydrochloric acid solution ranges from 0.10 mol/L to 1 mol/L, and a concentration of the sodium hydroxide solution ranges from 0.10 mol/L to 1 mol/L.

6. The method according to claim 5, wherein the reaction in S5 is conducted under reaction conditions as follows: a reaction temperature is 25° C., and a second reaction time is 24 hours; and the cleaning comprises sequentially cleaning with absolute ethyl alcohol and ultrapure water.

7. The method according to claim 3, wherein in S4, a hydrophobic silane coupling agent in the hydrophobic silane coupling agent solution is one of trimethoxymethylsilane, ethyltrimethoxysilane, trimethoxy(propyl)silane, trimethoxyphenylsilane or hexadecyltrimethoxysilane, a solvent in the hydrophobic silane coupling agent solution is toluene, and a concentration range of the hydrophobic silane coupling agent in the hydrophobic silane coupling agent solution is 1 g/L to 50 g/L.

* * * * *